(12) United States Patent
Sayag et al.

(10) Patent No.: US 12,324,626 B2
(45) Date of Patent: Jun. 10, 2025

(54) PROCESS FOR DETERMINING OPHTHALMIC PARAMETERS BY 3D MAPPING

(71) Applicant: ACEP FRANCE, Paris (FR)

(72) Inventors: Jean-Philippe Sayag, Paris (FR); Alexander Shelymagin, Vilnius (LT)

(73) Assignee: ACEP FRANCE, Paris (FR)

( * ) Notice: Subject to any disclaimer, the term of this patent is extended or adjusted under 35 U.S.C. 154(b) by 540 days.

(21) Appl. No.: 17/618,085

(22) PCT Filed: Jun. 10, 2020

(86) PCT No.: PCT/EP2020/066140
§ 371 (c)(1),
(2) Date: Dec. 10, 2021

(87) PCT Pub. No.: WO2020/249643
PCT Pub. Date: Dec. 17, 2020

(65) Prior Publication Data
US 2022/0296096 A1    Sep. 22, 2022

(30) Foreign Application Priority Data

Jun. 11, 2019 (FR) ...................................... 1906179

(51) Int. Cl.
*A61B 3/10* (2006.01)
*A61B 3/00* (2006.01)
(Continued)

(52) U.S. Cl.
CPC ............ *A61B 3/111* (2013.01); *A61B 3/0025* (2013.01); *A61B 3/10* (2013.01); *A61B 3/112* (2013.01);
(Continued)

(58) Field of Classification Search
CPC ......... A61B 3/111; A61B 3/0025; A61B 3/10; A61B 3/112; A61B 3/14; A61B 2560/0406; G02C 13/003; G02C 13/005
(Continued)

(56) References Cited

U.S. PATENT DOCUMENTS

| 9,395,562 B1 | 7/2016 | Nguyen et al. |
| 9,618,620 B2 | 4/2017 | Zweigle et al. |

(Continued)

FOREIGN PATENT DOCUMENTS

| DE | 102005003699 A1 | 7/2006 |
| DE | 102011009646 A1 | 8/2012 |

(Continued)

OTHER PUBLICATIONS

International Search Report and Written Opinion issued on Sep. 8, 2020 in corresponding International Application No. PCT/EP2020/066140; 12 pages.

(Continued)

*Primary Examiner* — Mahidere S Sahle
(74) *Attorney, Agent, or Firm* — Maier & Maier, PLLC

(57) ABSTRACT

A method for determining ophthalmic parameters for a given frame and a given wearer, including: a) the given wearer is fitted with said given frame; b) providing a device including a first projecting mean able to project a pattern of optical radiation onto the face of the wearer, a first camera able to record said pattern of optical radiation, a processing device able to processes the image of the pattern in order to generate a depth map of the face of the wearer, a screen able to display the images recorded by said first camera and a light source able to illuminate the pupils of the wearer, c) recording simultaneously a depth map of the face of the wearer and a picture of the face of the wearer while said light source is illuminating the pupils of the wearer.

14 Claims, 4 Drawing Sheets

(51) Int. Cl.
  *A61B 3/04* (2006.01)
  *A61B 3/11* (2006.01)
  *A61B 3/14* (2006.01)
  *G02C 13/00* (2006.01)
(52) U.S. Cl.
  CPC .............. *A61B 3/14* (2013.01); *G02C 13/003* (2013.01); *G02C 13/005* (2013.01); *A61B 2560/0406* (2013.01)
(58) Field of Classification Search
  USPC .......................... 351/204, 206, 208, 227, 246
  See application file for complete search history.

(56) References Cited

U.S. PATENT DOCUMENTS

| | | | |
|---|---|---|---|
| 10,107,914 B2 | 10/2018 | Kalscheur et al. | |
| 11,126,016 B2 | 9/2021 | Breuninger et al. | |
| 11,195,318 B2 | 12/2021 | Suma et al. | |
| 2009/0021693 A1 | 1/2009 | Sessner et al. | |
| 2014/0152956 A1* | 6/2014 | Silva .................... | G02C 13/003 351/204 |
| 2015/0146168 A1 | 5/2015 | Divo et al. | |
| 2016/0299360 A1 | 10/2016 | Sone et al. | |
| 2017/0336654 A1* | 11/2017 | Seitz .................... | G02C 13/005 |
| 2018/0321517 A1 | 11/2018 | El-Hajal et al. | |
| 2019/0033624 A1* | 1/2019 | Breuninger .......... | G02C 13/005 |
| 2020/0292307 A1* | 9/2020 | Seitz .................... | G01B 11/002 |
| 2022/0218198 A1* | 7/2022 | Devani ................ | A61B 5/4088 |

FOREIGN PATENT DOCUMENTS

| | | | |
|---|---|---|---|
| DE | 102014015671 A1 | 4/2016 | |
| DE | 102015001874 A1 | 8/2016 | |
| DE | 102016106121 A1 | 10/2017 | |
| EP | 2772795 A1 | 9/2014 | |
| EP | 3413122 A1 | 6/2017 | |
| EP | 3270099 A1 | 1/2018 | |

OTHER PUBLICATIONS

International Preliminary Report on Patentability issued on Aug. 5, 2021, in corresponding International Application No. PCT/EP2020/066140; 12 pages.
In the United States District Court for the Southern District of Florida Miami Division; *Optikam Tech Inc., Plaintiff*, vs. *American Bright Signs, Inc.* (dba ACEP USA), ACEP Group, and ACEP France Defendants; Civil Action No. 1:23-cv-23597-RAR/JB; "Expert Report of John R. Grindon, D.Sc. On The Invalidity of U.S. Pat. No. 11,579,472", Sep. 13, 2024, 125 pages.
Feng, et al., "Rapid Avatar Capture and Simulation Using Commodity Depth Sensors", USC Institute for Creative Technologies, University of Southern California, May 23, 2014, 1 page.
Chmiel, "How to Create a Measuring App With ARKit In IOS 11" by Pawel Chmiel, Droids on Roids, Jul. 13, 2017, 11 pages URL: https://www.thedroidsonroids.com/blog/how-to-create-a-measuring-app-with-arkit-in-ios-11 Archive: https://web.archive.org/web/20200415023503/https://www.thedroidsonroids.com/blog/how-to-create-a-measuring-app-with-arkit-in-ios-11.
Pereira, "ARKit introduction" by Ricardo Pereira, Whitesmith, Jul. 19, 2017, 12 pages URL: https://www.whitesmith.co/blog/arkit-introduction/ Archive: https://web.archive.org/web/20200415023503/https://www.whitesmith.co/blog/arkit-introduction/.
Apple Developer, Apple developer documentation entry for the VNFaceLandmarks2D class,"VNFaceLandmarks2D", Jun. 18, 2019, 4 pages URL: https://developer.apple.com/documentation/vision/vnfacelandmarks2d Archive: https://web.archive.org/web/20190618115314/https://developer.apple.com/documentation/vision/vnfacelandmarks2d.
Quora, "How can Apple's ARKit (Augmented Reality) do precise measurement with just one camera?", Quora, Inc. Jan. 10, 2025, 14 pages URL: https://www.quora.com/How-can-Apple%E2%80%99s-ARKit-Augmented-Reality-do-precise-measurement-with-just-one-camera.
Intel Realsense, "Room Scanning using LiDAR Camera L515 Demo", Youtube, Jan. 27, 2020, 1 page URL: https://youtu.be/41Yu2H9_z3w?si=daIDOXg5R1Q-qWRk Archive: https://web.archive.org/web/20200720225936/https://www.youtube.com/watch?v=41Yu2H9_z3w.
Intel Realsense, "Body Scanning using LiDAR Camera L515", Youtube, Jan. 27, 2020, 1 page URL: https://www.youtube.com/watch?v=Uzlfn667abE Archive: https://web.archive.org/web/20201104074949/https://www.youtube.com/watch?v=Uzlfn667abE&feature=youtu.be.
Intel Realsense, "Intel RealSense LiDAR Camera L515—the worlds' smallest high-resolution LiDAR depth camera", Youtube, Dec. 11, 2019, 1 page URL: https://www.youtube.com/watch?v=Rx-75ZEAMeg Archive: https://web.archive.org/web/20200225090525/https://www.youtube.com/watch?v=Rx-75ZEAMeg.
Intel Realsense, Intel RealSense Depth and Tracking Cameras, store, "Intel Realsense LiDAR Camera L515", Jan. 7, 2020, 5 pages Archive: http://web.archive.org/web/20200107220737/https://www.intelrealsense.com/lidar-camera-l515/.
Optikam Tech, "Optikam Pad Product Demo", Vimeo, Uploaded Jan. 3, 2015, 1 page URL: https://vimeo.com/115857055.
Optikam Tech, "Spectangle Pro Product Demo", Vimeo, Uploaded Mar. 6, 2015, 1 page URL: https://vimeo.com/121471286.
Optikam Tech, "OptikamPad Training Video", Vimeo, Uploaded Feb. 6, 2013, 1 page URL: https://vimeo.com/59100367.
Optikam Tech, "The OptikamPad Experience", Vimeo, Uploaded Mar. 15, 2015, 1 page URL: https://vimeo.com/122272236.
Goldberg, "Putting virtual glasses on a real face: Warby Parker's Virtual Try-On placement algorithm", Medium, Apr. 2, 2019, 12 pages URL: https://medium.com/@davidhgoldberg/putting-virtual-glasses-on-a-real-face-warby-parkers-virtual-try-on-placement-algorithm-beb1e81c1d62 Archive: https://web.archive.org/web/20190409190101/https://medium.com/@davidhgoldberg/putting-virtual-glasses-.
Optikam Tech, "The Spectangle Pro Experience Video", Vimeo, Uploaded Nov. 5, 2015, 1 page URL: https://vimeo.com/1447949.
Optikam Tech, Spectangle Pro Training Video, VImeo, Feb. 6, 2015, 1 page URL: https://vimeo.com/118945207.
Optikam Tech, Optikam Tech Vimeo Channel (Various), Vimeo, 1 page URL: https://vimeo.com/user16311401.
*Optikam Tech Inc.* v. *American Bright Signs, Inc.* (dba ACEP USA), ACEP Group, and ACEP France, U.S. District Court for the Southern District of Florida, No. 1:23-cv-23597-RAR/JB, Sep. 14, 2024, 250 pages.
Technology for Opticians, "SmartMIRROR V1 Measurements", Youtube, Uploaded Aug. 12, 2017, 1 page URL: https://www.youtube.com/watch?v=fWttBLfAZzc.
ACEPdirect, "SmartMirror for Ipad", Facebook, Uploaded Jul. 20, 2015, 1 page URL: https://www.facebook.com/photo/?fbid=492989864186693&set=smart-mirror-for-ipadsmart-mirror-works-on-the-ipad-mini-ipad-mini-2-ipad2-ipad4.

\* cited by examiner

[Fig. 1]

[Fig. 2]

[Fig. 3]

[Fig. 4]
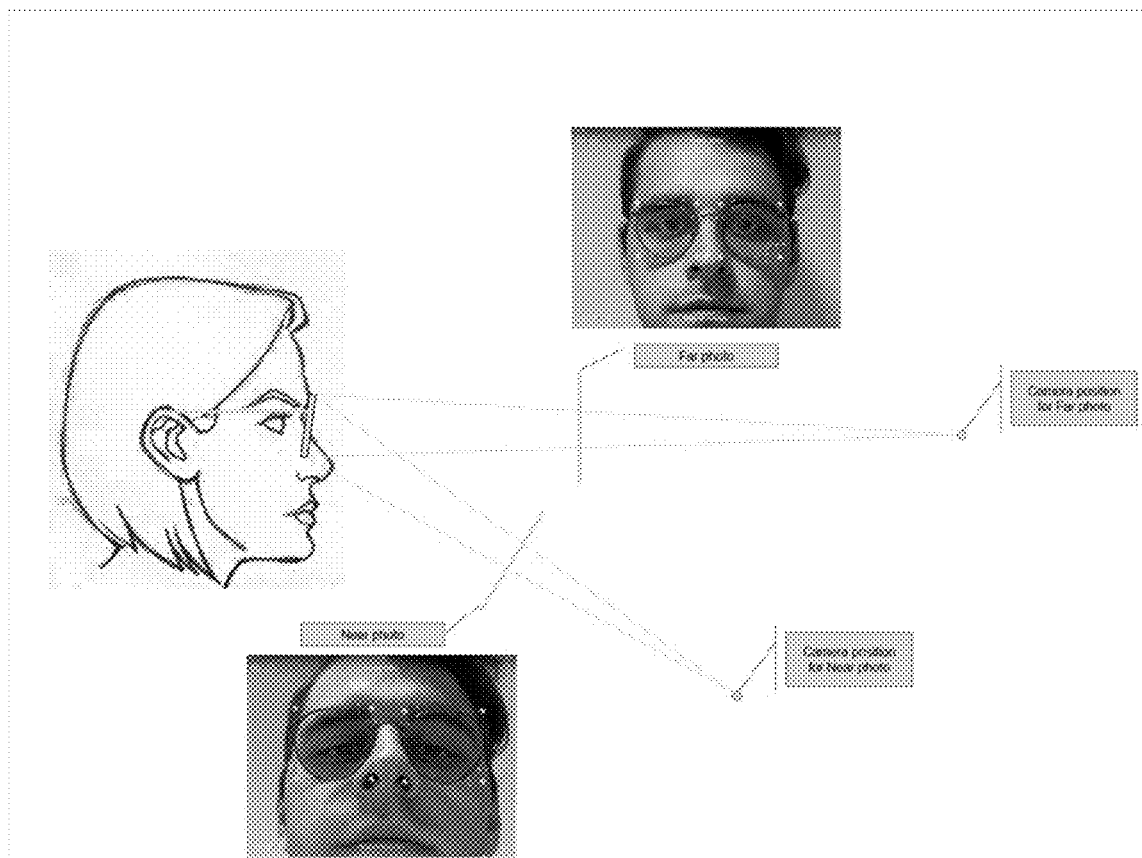

PROCESS FOR DETERMINING OPHTHALMIC PARAMETERS BY 3D MAPPING

BACKGROUND

The present invention relates to a device for measuring the various ophthalmic parameters of a patient. The present invention also relates to a process for measuring the various ophthalmic parameters of a patient by using the device according to the invention.

Measurement of ophthalmic parameters have traditionally been performed using Frame Reference Devices (FREDs). The FREDs main function is to provide scale to the image of the customer wearing a new frame, and also to indicate head rotation and pantoscopic tilt. Some manufacturers added more functions to FREDs allowing them to measure back vertex distance (BVD), frame vertical size (B size), or frame wrap angle.

FREDs are used in combination with a camera able to take a picture of the head of the patient wearing a pair of spectacles associated with the FRED. For example, an image of the patient is taken, under conditions of extended vision. The peaks of the cornea of the patient's eyes reflect light from a known source and produce two reflections in the form of two well defined lighter colored dots. Then, a computer program is able to determine the distance between the two dots from a distance defined by the scale present on the FRED. The computer program includes a routine image processing which determines the number of pixels corresponding to the length of the scale and the number of pixels that separate the two dots, and then knowing the length of the scale, it calculates the distance between the two pupils.

However, FREDs suffer from many drawbacks. They are cumbersome, not very attractive, and sometimes hard to attach to the frame in the right way. Moreover, they can be damaged or being lost and then have to be replaced.

For these reasons, there is a need for a process for centration measurements without using FRED.

Some "column" fixed-type system exist that offer measurements without FRED. For this purpose, calibrated camera systems and fixed customer positioning have to be used. However, such columns are cumbersome and expensive.

To date, there is no known solution that would provide centration measurement without FRED on a tablet or a mobile platform which would be a more versatile and affordable solution.

SUMMARY

With this respect, the present invention provides a mobile apparatus that allows determining optical parameters such as pupillary distance without the need of external scales such as FREDs. Moreover, the apparatus and process according to the invention allow measuring the optical parameters at the normal reading distance and at the far sightseeing distance.

To this end, the present invention provides a method for determining ophthalmic parameters for a given frame and a given wearer, said method comprising the following steps:
a) said given wearer is fitted with said given frame;
b) providing a device comprising a first projecting mean able to project a pattern of optical radiation onto the face of the wearer, a first camera able to record said pattern of optical radiation, a processing device able to process the image of the pattern in order to generate a depth map of the face of the wearer, a screen able to display the images recorded by said first camera, and a light source able to illuminate the pupils of the wearer,
c) recording simultaneously a depth map of the face of the wearer and a picture of the face of the wearer while said light source is illuminating the pupils of the wearer,
d) determining automatically the position of the pupils of the wearer,
e) associating the position of the pupils of the wearer to their respective coordinates in the 3D depth map,
f) determining from the respective coordinates of the pupils of the wearer said ophthalmic parameters.

According to a preferred embodiment of the invention, said device is a mobile device (e.g. a tablet or a smartphone). According to an alternative embodiment, said device is a column.

According to a preferred embodiment of the invention, the process according to the invention further comprises before step c) a step comprising the determination of the direction of gaze of the wearer from a depth map obtained by illuminating the face of the wearer by the first projecting mean with a pattern of optical radiation and by recording a second picture comprising said pattern.

According to a preferred embodiment of the invention, the process according to the invention further comprises before step c) a step comprising the determination of the head inclination of the wearer from a depth map obtained by illuminating the face of the wearer by the first projecting mean with a pattern of optical radiation and by recording a second picture comprising said pattern.

According to a preferred embodiment, the method according to the invention further comprises a step wherein the position of the pupils obtained at step d) is displayed on the screen with said recorded image of the face of the wearer and wherein said position can be corrected.

According to a preferred embodiment, the method according to the invention further comprises a step wherein the position of said frame is calculated from the recorded image of the face of the wearer and said position is associated to its respective coordinate in the 3D depth map.

According to a preferred embodiment, the method according to the invention further comprises a step where the position of said frame is displayed on the screen with said recorded image of the face of the wearer and wherein said position can be corrected.

According to a preferred embodiment, said optical parameters are chosen from the group comprising far vision pupillary distance, near vision pupillary distance, vertex, pantoscopic tilt, frame wrap, near vision fitting height and far vision fitting height.

According to a preferred embodiment, the wearer is holding said mobile device at an arm length and at eye level.

According to another preferred embodiment, the wearer is holding said mobile device at a reading distance.

According to a preferred embodiment, said screen displays a focusing point while step c).

According to a preferred embodiment, said screen displays a transversal line while step c).

According to a preferred embodiment, said light source is obtained by displaying a white form on said screen while step c).

According to a preferred embodiment, said screen displays the image recorded by said camera.

The present invention also provides a device, preferably a mobile device, comprising a first projecting mean able to project a pattern of optical radiation onto the face of an individual wearing a frame, a first camera able to record said pattern of optical radiation, a processing device able to process the image of the pattern in order to generate a depth map of the face of said individual, a screen able to display the images recorded by said first camera, a light source able to illuminate the pupils of the wearer wherein said device further comprises a software able to implement a process according to the invention.

BRIEF DESCRIPTION OF THE FIGURES

FIG. 1 is a picture of a user holding the mobile device according to the invention at an arm length.

FIG. 2 is a screenshot of the screen displayed by the mobile device according to the invention while recording a picture of the user's face.

FIG. 3 is a picture of a user holding the mobile device according to the invention in a reading position.

FIG. 4 illustrates the combination of a far vision depth map with a reading position depth map to calculate vertex and pantoscopic tilt.

DETAILED DESCRIPTION

The present invention provides a process and a mobile device able to determine the optical parameters of a wearer of a frame without using external calibration references. The wearer can use the mobile device according to the invention without the need of an external help.

The process according to the invention can be divided into two main phases. A first phase, in which the wearer use the mobile device according to the invention at an arm length in order to measure his optical parameters at a far sight distance. A second phase, wherein the wearer hold the mobile device according to the invention as a book in order to measure his optical parameters at a reading distance.

The process according to the invention is based on 3D mapping ability to measure distance with high precision. 3D mapping is obtained by a set of several equipment components working jointly to scan the surrounding continuously while the camera is active to build a depth map. Thanks to the 3D mapping precise distance measurements of points of interest on the customer picture, it is possible to put the customer image in scale, and perform centration measurements with good precision.

This set of equipment able to produce a depth map is provided, for example, in smartphone or tablet. With this respect, the mobile device according to the invention preferably comprises a smartphone or a tablet and the software able to implement the process according to the invention is a smartphone application.

In order to produce a depth map, the apparatus according to the invention comprises a first projecting mean able to project a pattern of optical radiation onto the body (or at least parts of the body) of the patient. According to a preferred embodiment, the optical radiation used for this purpose is typically in the infrared (IR) range.

In order to capture an image of the patient with the optical radiation pattern, the apparatus according to the invention further comprises a first camera. Preferably, the optical axis of the first projection mean is parallel to the optical axis of said first camera. Furthermore, said first camera comprises a sensor able to record the optical radiation emitted by said first projection mean.

In order to process the image recorded by said first camera, the apparatus according to the invention further comprises a processing device able to processes the image of the pattern in order to generate a depth map of the body, i.e., an array of 3D coordinates, comprising a depth (Z) coordinate value of the body surface at each point (X, Y) within a predefined area.

For example, the processing device computes the 3D coordinates of points on the surface of the patient's face by triangulation.

Alternatively, the apparatus according to the invention can comprise a first camera able to record said optical radiation pattern and a second camera able to capture an image of the patient. In this embodiment, the processing device super-imposes the images produced by the two cameras in order to produce said depth map.

Furthermore, the processing device is advantageously able to processes the data generated in order to extract 3D image information.

According to a preferred embodiment, the processing device is able to identify parts of the face of the patient such as the internal corner of the eyes, the pupils centre, the middle of the forehead, and/or the middle of the chin and determine their 3D locations.

According to an even more preferred embodiment, the processing device is able to identify parts of the spectacles worn by the patient and determine their 3D location.

The apparatus according to the invention also comprises a screen able to display the images recorded by one of the camera of said apparatus and/or user's information. According to a preferred embodiment of the invention, said screen is a touchscreen.

For the production of a depth map of a patient, an illumination pattern illuminates the face of said with an appropriate pattern. For this purpose, the first projection means typically comprises a suitable radiation source, and optics, such as a diffuser or a diffractive optical element, for creating the pattern.

The first camera or the first and the second camera record an image of the pattern on the patient's face. First and second camera typically comprises an optic, which image the patient's face onto a sensor.

As previously explained, the radiation source typically emits IR radiation, but other radiation bands, in the visible or ultraviolet range may also be used. When IR radiation are used, the sensor may comprise a monochrome image sensor, without an IR-cut-off filter, in order to detect the image of the projected pattern with high sensitivity.

The processing device receives and processes image inputs from said camera. Said processing device compares the recorded image to a reference image of the pattern projected onto a plane, at a known distance. The processing device matches the local patterns in the recorded image to those in the reference image and thus finds the transverse shift for each pixel. Based on these transverse shifts and on the known distance the processing device computes a depth (Z) coordinate for each pixel.

The device according to the invention further comprises a light source able to illuminate the pupils of the user in order to produce bright (e.g. white) spots, which will be detected by the device according to the invention. According to a preferred embodiment of the invention, said light source is an electronic flash. According to another preferred embodiment said light source is produced by said screen. According to a more preferred embodiment, said light source is produced by displaying a bright (e.g. white) shape, preferably a parallelepiped or a circle, on the screen.

According to a first embodiment of the invention, in order to produce optical parameters measurements at a far sight distance, the wearer of the frame hold the mobile device according to the invention with one or preferably both his hands stretched (see [FIG. 1]).

In order to help the wearer to put the mobile device according to the invention at the right level (i.e. at the eyes level), the screen of said mobile device preferably displays in real time the image recorded by said camera superimposed with a transversal horizontal line. Said horizontal line can be used as a target by the wearer. The correct positioning of the mobile device according to the invention is obtained by aligning the image of the eyes of the wearer with said horizontal line.

According to a more preferred embodiment, the device according to the invention is able to display a signal to the user when the face, the eyes and the frame are correctly positioned toward said device. Accordingly, the process according to the invention further comprises a step wherein said device displays a signal to the user when his face, his frame and/or his eyes are correctly positioned toward said device. Moreover, the software able to implement the process according to the invention can restrict the further progress of the process according to the invention until the face, the frame and/or the eyes are correctly positioned.

According to a further preferred embodiment of the invention, the mobile device according to the invention comprises a gyroscope or a digital accelerometer able to determine the vertical inclination of said mobile device. According to this embodiment said information is provided, via said screen, to the wearer in order to help him to hold said mobile device vertical. Alternatively, the software able to implement the process according to the invention can restrict the further progress of the process according to the invention until said mobile device is vertical. The position of said horizontal line on the screen can be calculated by said processing device by computing the distance from the camera to the screen of the mobile device, the orientation of said camera, the vertical orientation or horizontal orientation of said mobile device.

According to a preferred embodiment of the invention, the head inclination of the wearer is determined from a depth map obtained by illuminating the face of the wearer by the first projecting mean with a pattern of optical radiation and by recording a second picture comprising said pattern as previously explained. According to a more preferred embodiment the head inclination of the wearer is determined continuously at least until said head inclination is equivalent to the natural head inclination. As used herein the term "equivalent" means that the head inclination of the wearer is within −12-+12 deg range of a natural head inclination, According to this embodiment said information is provided, via said screen, to the wearer in order to modify his head inclination. Alternatively, the software able to implement the process according to the invention can restrict the further progress (into step c)) of the process according to the invention until said head inclination is equivalent to a natural head inclination.

The measurement of the ophthalmic parameters of the wearer when his head inclination is natural allows to obtain optimal results.

According to a preferred embodiment of the invention, the direction of gaze of the wearer is determined from a depth map obtained by illuminating the face of the wearer by the first projecting mean with a pattern of optical radiation and by recording a second picture comprising said pattern as previously explained. According to a preferred embodiment of the invention, the inclination of the mobile device (provided by on-board accelerometer) is used in combination with said depth-map to determine said direction of gaze.

According to a more preferred embodiment the direction of gaze of the wearer is determined continuously at least until said gaze is horizontal, According to this embodiment said information is provided, via said screen, to the wearer in order to modify his direction of gaze. Alternatively, the software able to implement the process according to the invention can restrict the further progress (into step c)) of the process according to the invention until said direction of gaze is horizontal.

When the position of the mobile device and head inclination are correct, the wearer can start the measurement by pressing a dedicated position of the screen. Alternatively, said measurement process can be induced by any other means. For example, the mobile device according to the invention can comprise a microphone able to transmit the sounds, emitted by the wearer, to the processing device. With this respect, the measurement process can be induced via the emission of a specific word.

The measurement process comprises the step of simultaneously taking a picture of the face of the wearer and a depth map of said face. In order to help the discrimination of the pupils by the processing device, the picture of the face of the wearer is taken while a light source is illuminating his pupils. This light source might be an electronic flash or preferentially, the reflection on the pupils is obtained by displaying on the screen a light colored shape (e.g. a white shape). According to a preferred embodiment, said shape covers 40 to 100% of the screen's surface. Moreover, while recording the picture of the wearer's face, the screen of the mobile device according to the invention is preferentially displaying a target (i.e. a focusing point) near the position of the camera and the user is invited to look at this target (see [FIG. 2]). According to a preferred embodiment of the invention, said target is red and even more preferably is a red circle.

Alternatively, it can be advantageous to shift said target to the right, to the left, above or below said camera in order to make the eyes and/or the head of the wearer move to follow the target. This specific embodiment of the invention allows to determine the dominant eye, the ocular mobility and/or the head mobility of the wearer.

While this picture is recorded by the camera, the face of the wearer is also illuminated by the first projecting mean with a pattern of optical radiation and a second picture comprising said pattern is recorded. As both pictures have been taken simultaneously, they can be superimposed, and each pixels of the first picture can be associated to a precise geographic location via the depth map calculated from the second picture.

The processing device automatically detects pupils centers from the first picture. The one skilled in the art of image processing knows how to detect such points. For example, the pixels corresponding to the pupils centers can be discriminated from the pixels surrounding them by their specific color.

In a preferred embodiment, the picture of the face is displayed with the automatically detected positions of the pupils. Thus, these positions can be corrected, when needed, by the user. The correction of the position is preferably made by using the touchscreen when available.

As soon as the exact positions of the pupils centers are validated by the user, the processing device can calculate the distance between each pupils from their respective positions on the depth map. The optical parameters are then preferably displayed on the screen and recorded with or without the depth map and the picture of the face of the wearer in a storage device. With this respect, the mobile device according to the invention further comprises a storage media.

Furthermore, the processing device automatically detects the position of the frame's rims from the first picture and/or from the depth map. The one skilled in the art of image processing knows how to detect such positions. For example, the pixels corresponding to the rim have the same color and form a geometric shape that can be discriminated from the pixels surrounding them. The position of the rims can also be deduced from the depth maps as the rims form a geometrical shape enclosed in a vertical plane in front of the wearer's face.

According to a preferred embodiment of the invention, the positions of the pupils used for the calculation of the ophthalmologic parameters can be corrected in order to take into account the convergence of the eyes on the device according to the invention. This correction can be made by using the distance, between the device according to the invention and the eyes, provided by the depth map.

In a preferred embodiment, the picture of the face is displayed with the automatically detected positions of the rims. Thus, these positions can be corrected, when needed, by the user. The correction of the position is preferably made by using the touchscreen when available.

As soon as the exact positions of the rims and of the pupils centers are validated by the user, the processing device can calculate the distance between each pupils and their respective rims, from their respective positions on the depth map. Preferably, the distance between the pupil and the lower edge of its respective rim is calculated.

According to a second embodiment of the invention, in order to produce optical parameters measurements at a reading distance, the wearer of a frame holds the mobile device according to the invention with one or both his hands in a natural reading position (see [FIG. 3]).

The remaining part of the process is identical to the one disclosed above.

In order to calculate more optical parameters, such as pantoscopic tilt and vertex, the process according to the invention use a combination of the depth map and the picture recorded at a far sight distance with the depth map and the picture recorded at a reading distance.

According to this further embodiment of the invention, the process according to the invention comprises a step where a 3D scene is reconstructed from the picture obtained at far sight distance and the picture obtained at a reading distance. Methods to create a 3D scene form two 2D pictures is well known to the one skilled in the art of computer vision and can be implemented easily in the processing device comprised in the mobile device according to the invention. Examples of said methods are available, for example, at https://en.wikipedia.org/wild/3D_reconstruction.

The two pictures can be related to one another by using cardinal points detected on the wearer's face. Among these points, the middle of the forehead and the middle of the chin are preferred.

The process for calculating pantoptic tilt and vertex from this reconstructed 3D scene is illustrated in [FIG. 4] and comprises the following steps:

determination of the top frame point position in 3D scene and bottom frame point position in 3D scene,
construction of a first line from camera position for far sight picture photo to top frame point on the far sight photo projection,
construction of a second line from camera position for reading distance picture to top frame point on reading distance picture projection
determination of the top frame point position in the 3D scene from the point of intersection of said first and second lines,
construction of a third line from camera position for far sight picture photo to bottom frame point on the far sight photo projection,
construction of a fourth line from camera position for reading distance picture to bottom frame point on reading distance picture projection
determination of the bottom frame point position in the 3D scene from the point of intersection of said third and fourth lines.

The pantoscopic tilt and the vertex can then be directly determined form the exact position.

The invention claimed is:

1. A method for determining ophthalmic parameters for a given frame and a given wearer, said method comprising the following steps:
a) fitting said given wearer with said given frame;
b) providing a mobile device comprising a first projecting mean able to project a pattern of optical radiation onto the face of the wearer, a first camera able to record said pattern of optical radiation, a processing device able to processes the image of the pattern in order to generate a depth map of the face of the wearer, a screen able to display the images recorded by said first camera and a light source able to illuminate the pupils of the wearer,
c) recording simultaneously a depth map of the face of the wearer and a picture of the face of the wearer while said light source is obtained by displaying a white form on said screen and is illuminating the pupils of the wearer while said screen displays a focusing point,
d) determining automatically the position of the pupils of the wearer,
e) associating the position of the pupils of the wearer to their respective coordinates in the depth map,
f) determining from the respective coordinates of the pupils of the wearer said ophthalmic parameters, and
further comprising a step wherein the position of the pupils obtained at step d) is displayed on the screen with said recorded image of the face of the wearer and wherein said position can be corrected.

2. The method according to claim 1 further comprising a step wherein the position of said frame is calculated form the recorded image of the face of the wearer and said position is associated to its respective coordinate in the depth map.

3. The method according to claim 1 further comprising a step where the position of said frame is displayed on the screen with said recorded image of the face of the wearer and wherein said position can be corrected.

4. The method according to claim 1 wherein said optical parameters are chosen from the group comprising far vision pupillary distance, near vision pupillary distance, vertex pantoscopic tilt, frame wrap, near vision fitting height and far vision fitting height.

5. The method according to claim 1, wherein the wearer is holding said mobile device at an arm length and at eye level.

6. The method according to claim 1, wherein the wearer is holding said mobile device at a reading distance.

7. The method according to claim 1, further comprising, before step c), determining the direction of gaze of the wearer from a depth map obtained by illuminating the face of the wearer by the first projecting mean with a pattern of optical radiation and by recording a second picture comprising said pattern.

8. The method according to claim 1, further comprising, before step c), determining the head inclination of the wearer from a depth map obtained by illuminating the face of the wearer by the first projecting mean with a pattern of optical radiation and by recording a second picture comprising said pattern.

9. The method according to claim 1, wherein said focusing point is a red circle.

10. The method according to claim 1, wherein said focusing point is near said camera.

11. The method according to claim 1, wherein said focusing point is shifted to the right, to the left, above or below said camera.

12. The method according to claim 1, wherein said screen displays a transversal line while step c).

13. The method according to the screen to claim 1, wherein said screen displays the image recorded by said camera.

14. A mobile device, comprising a first projecting mean able to project a pattern of optical radiation onto the face of an individual wearing a frame, a first camera able to record said pattern of optical radiation, a processing device able to process the image of the pattern in order to generate a depth map of the face of said individual, a screen able to display the images recorded by said first camera, a light source able to illuminate the pupils of the wearer wherein said mobile device further comprises a software able to implement a process according to claim 1.

* * * * *